US011053534B2

(12) United States Patent
Fryer et al.

(10) Patent No.: US 11,053,534 B2
(45) Date of Patent: Jul. 6, 2021

(54) SYSTEMS AND METHODS FOR CONFIRMING ACTIVATION OF BIOLOGICAL INDICATORS (71) Applicant: ASP Global Manufacturing GmbH, Schaffhausen (CH)

(72) Inventors: Ben Fryer, Lake Forest, CA (US); Yan Fang, Irvine, CA (US)

(73) Assignee: ASP GLOBAL MANUFACTURING GMBH, Schaffhausen (CH)

(*) Notice: Subject to any disclaimer, the term of this patent is extended or adjusted under 35 U.S.C. 154(b) by 136 days.

(21) Appl. No.: 15/639,872

(22) Filed: Jun. 30, 2017

(65) Prior Publication Data
US 2019/0002951 A1   Jan. 3, 2019

(51) Int. Cl.
*C12Q 1/22* (2006.01)
*G01N 21/64* (2006.01)
*A61L 2/28* (2006.01)

(52) U.S. Cl.
CPC .................. *C12Q 1/22* (2013.01); *A61L 2/28* (2013.01); *G01N 21/6428* (2013.01); *G01N 2021/6432* (2013.01)

(58) Field of Classification Search
None
See application file for complete search history.

(56) References Cited

U.S. PATENT DOCUMENTS

| | | |
|---|---|---|
| 3,346,464 A | 10/1967 | Ernst |
| 3,752,743 A | 8/1973 | Henshilwood |
| 3,948,727 A | 4/1976 | Steiger |
| 4,291,122 A | 9/1981 | Orelski |
| 4,304,869 A | 12/1981 | Dyke |
| 4,528,268 A | 7/1985 | Andersen et al. |
| 4,546,086 A | 10/1985 | Hounsell |
| 4,717,661 A | 1/1988 | McCormick et al. |
| 4,732,850 A | 3/1988 | Brown et al. |
| 4,839,291 A | 6/1989 | Welsh et al. |
| 4,883,641 A | 11/1989 | Wicks et al. |
| 4,885,253 A | 12/1989 | Kralovic |
| 5,028,543 A | 7/1991 | Finch et al. |
| 5,073,488 A | 12/1991 | Matner et al. |
| 5,167,923 A | 12/1992 | Van Iperen |
| 5,223,401 A | 6/1993 | Foltz et al. |
| 5,252,484 A | 10/1993 | Matner et al. |
| 5,362,654 A | 11/1994 | Pouletty |
| 5,405,580 A | 4/1995 | Palmer |
| 5,415,994 A | 5/1995 | Imrich et al. |
| 5,418,167 A | 5/1995 | Matner et al. |
| 5,482,171 A | 1/1996 | Palmer |
| 5,516,648 A | 5/1996 | Malchesky et al. |
| 5,552,320 A | 9/1996 | Smith |
| 5,736,355 A | 4/1998 | Dyke et al. |
| 5,739,004 A | 4/1998 | Woodson |
| 5,750,184 A | 5/1998 | Imburgia |
| 5,759,848 A | 6/1998 | Nagoshi et al. |
| 5,770,393 A | 6/1998 | Dalmasso et al. |
| 5,801,010 A | 9/1998 | Falkowski et al. |
| 5,830,683 A | 11/1998 | Hendricks et al. |
| 5,863,790 A | 1/1999 | Bolea |
| 5,866,356 A | 2/1999 | Albert et al. |
| 5,942,438 A | 8/1999 | Antonoplos et al. |
| 6,218,189 B1 | 4/2001 | Antonoplos et al. |
| 6,436,659 B1 | 8/2002 | Hui et al. |
| 6,458,554 B1 | 10/2002 | Hui et al. |
| 6,551,555 B2 | 4/2003 | Antonoplos et al. |
| 6,924,139 B2 | 8/2005 | Eveland et al. |
| 7,091,042 B2 | 8/2006 | Lemus et al. |
| 7,247,482 B2 | 7/2007 | Lemus et al. |
| 7,642,067 B2 | 1/2010 | Song et al. |
| 8,173,388 B2 | 5/2012 | Pasmore et al. |
| 8,173,438 B1 | 5/2012 | Putnam et al. |
| 8,765,398 B2 | 7/2014 | Dalmasso |
| 8,840,837 B2 | 9/2014 | Smith et al. |
| 8,915,413 B2 | 12/2014 | Kayser |
| 8,945,837 B2 | 2/2015 | Franciskovich et al. |
| 8,969,029 B2 | 3/2015 | Chandrapati et al. |
| 8,980,622 B2 | 3/2015 | Smith |
| 9,145,573 B2 | 9/2015 | Pederson et al. |
| 9,322,046 B2 | 4/2016 | Chandrapati et al. |
| 9,675,722 B2 | 6/2017 | Ahimou et al. |
| 10,059,977 B2 | 8/2018 | Witcher et al. |
| 2004/0197848 A1* | 10/2004 | Behun ...................... C12Q 1/22 435/29 |
| 2005/0014214 A1 | 1/2005 | Eveland et al. |
| 2008/0070272 A1 | 3/2008 | Franciskovich et al. |
| 2009/0068716 A1 | 3/2009 | Hirota et al. |
| 2011/0200992 A1* | 8/2011 | Chandrapati ............ C12Q 1/22 435/6.1 |
| 2012/0149094 A1 | 6/2012 | Smith et al. |
| 2012/0156090 A1 | 6/2012 | Dane et al. |
| 2013/0210048 A1 | 8/2013 | Chandrapati et al. |
| 2013/0217107 A1 | 8/2013 | Pederson et al. |
| 2013/0224849 A1 | 8/2013 | Chandrapati et al. |

(Continued)

FOREIGN PATENT DOCUMENTS

| | | |
|---|---|---|
| CA | 738687 A | 7/1966 |
| CA | 823163 A | 9/1969 |

(Continued)

OTHER PUBLICATIONS

U.S. Appl. No. 15/057,768, filed Mar. 1, 2017.

(Continued)

*Primary Examiner* — Emily A Cordas
(74) *Attorney, Agent, or Firm* — Etan S. Chatlynne; Roberts Calderon Safran & Cole P.C.

(57) ABSTRACT

Biological indicators may be improperly activated. The disclosed subject matter is directed to methods of confirming that a biological indicator having an ampule containing a growth medium has been properly activated such that it may be assayed. The methods may include the steps of measuring a first fluorescence intensity of the biological indicator, heating the biological indicator; quenching the fluorescence intensity of the biological indicator from the first fluorescence intensity to a second fluorescence intensity, measuring the second fluorescence intensity; comparing the second fluorescence intensity and first fluorescence intensity to obtain a comparison value; and determining that the comparison value corresponds to a quenching metric of the liquid growth medium.

8 Claims, 4 Drawing Sheets

(56) References Cited

U.S. PATENT DOCUMENTS

| | | |
|---|---|---|
| 2015/0004682 A1 | 1/2015 | Smith et al. |
| 2015/0167047 A1 | 6/2015 | Smith et al. |
| 2015/0337354 A1* | 11/2015 | Ahimou .................. C12Q 1/22 435/31 |
| 2016/0000954 A1 | 1/2016 | Ahimou et al. |
| 2017/0175071 A1 | 6/2017 | Sullivan et al. |
| 2017/0211035 A1 | 7/2017 | Yirava et al. |
| 2018/0015193 A1 | 1/2018 | Swaminathan et al. |
| 2018/0071421 A1 | 3/2018 | Fang et al. |
| 2018/0237821 A1 | 8/2018 | Fryer |
| 2019/0106725 A1 | 4/2019 | Cregger et al. |
| 2019/0106726 A1 | 4/2019 | Cregger et al. |
| 2019/0169672 A1 | 6/2019 | Fryer et al. |

FOREIGN PATENT DOCUMENTS

| | | |
|---|---|---|
| CA | 1 182 729 A | 2/1985 |
| CN | 1853734 A | 11/2006 |
| CN | 201453688 U | 5/2010 |
| CN | 102596261 A | 7/2012 |
| CN | 203307339 U | 11/2013 |
| CN | 105087361 A | 11/2015 |
| CN | 204814967 U | 12/2015 |
| CN | 105561362 A | 5/2016 |
| CN | 106267277 A | 1/2017 |
| CN | 206473580 U | 9/2017 |
| CN | 206970617 U | 2/2018 |
| EP | 0152298 A2 | 8/1985 |
| EP | 1032822 B1 | 5/2003 |
| EP | 2968634 B1 | 12/2016 |
| FR | 2708287 B1 | 10/1995 |
| GB | 1055387 A | 1/1967 |
| IN | 201747012748 A | 4/2017 |
| IN | 201714046902 A | 7/2018 |
| JP | 10201466 A | 8/1998 |
| JP | 11196893 A | 7/1999 |
| JP | 2017123976 A | 7/2017 |
| JP | 2018201397 A | 12/2018 |
| RU | 129814 U1 | 7/2013 |
| RU | 146719 U1 | 10/2014 |
| RU | 2683644 C2 | 4/2019 |
| WO | 92/19764 A1 | 11/1992 |
| WO | 97/35189 A1 | 9/1997 |
| WO | 00/50634 A1 | 8/2000 |
| WO | 2005/036128 A2 | 4/2005 |
| WO | 2010/039388 A2 | 4/2010 |
| WO | 2010/045138 A2 | 4/2010 |
| WO | 2016/057520 A1 | 4/2016 |
| WO | 2016/205953 A1 | 12/2016 |
| WO | 2018025207 A1 | 2/2018 |
| WO | 2018/160449 A1 | 9/2018 |
| WO | 2008106327 A2 | 9/2018 |
| WO | 2020/136463 A1 | 7/2020 |

OTHER PUBLICATIONS

U.S. Appl. No. 15/397,018, filed Jan. 3, 2017.
Namsa, Self-Contained Biological Indicators For Monitoring Steam (Northwood, Ohio, 2015).
Anonymous, 3M™ ATTEST™ 1292E Rapid Readout Biological Indicator, Internet Article, Jan. 1, 1999, http://multimedia.3m.com/mws/mediawebserver?mwsId=SSSSSu7zK1fslxtU48_el8mGev7qe17zHvTSevTSeSSSSSS--&fn=Rapid_Readout_Profile_1292E.pdf.
Chinese First Office Action and Search Report for Chinese Patent Application No. 201810004516.1 dated Aug. 3, 2020 and English translation.
PCT Notification of Transmittal of the International Search Report and the Written Opinion of the International Searching Authority, or the Declaration for International Application No. PCT/IB2020/058750 dated Nov. 27, 2020, 1 page.
PCT Written Opinion of the International Searching Authority for International Application No. PCT/IB2020/058750 dated Nov. 27, 2020, 6 pages.
PCT International Search Report for International Application No. PCT/IB2020/058750 dated Nov. 27, 2020, 6 pages.

* cited by examiner

SYSTEMS AND METHODS FOR CONFIRMING ACTIVATION OF BIOLOGICAL INDICATORS

FIELD

The subject matter disclosed herein relates to self-contained biological sterilization indicators.

BACKGROUND

Medical devices are typically sterilized before use in order to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO). Each of these methods depends to a certain extent on the diffusion rates of the sterilization fluids, typically gases, upon the medical devices to be sterilized.

Before sterilization, medical devices are typically packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging helps prevent contamination of a sterile medical device, the packaging may increase the difficulty of achieving a successful sterilization cycle because the packaging impedes the sterilant from reaching the device or instrument contained therein. This is particularly problematic for devices and instruments that have diffusion-restricted spaces therein because these diffusion-restricted spaces reduce the likelihood that a sterilization cycle may be effective. For example, endoscopes typically have long narrow lumens into which the sterilant must diffuse in sufficient concentration for sufficient time to achieve a successful sterilization cycle.

Confirming that a sterilization cycle has been efficacious helps medical personnel avoid using a contaminated medical device on a subject. Typically, the sterilized medical device is not itself checked for contaminating organisms because such an activity would introduce other contaminating organisms to the medical device, thereby re-contaminating it. Thus, an indirect check has been developed in the form of a sterilization indicator.

A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms possessing known resistance to the sterilant may be placed into a sterilization chamber alongside a medical device and subjected to a sterilization cycle. After the cycle is complete, the microorganisms in the biological indicator may be cultured to determine whether any of the microorganisms survived the cycle.

Certain biological indicators are referred to as being "self-contained." These biological indicators typically include a housing that contains a quantity of microorganisms and a source of growth media in a frangible container that is located near the microorganisms. Like other biological indicators, the "self-contained" biological indicator ("SCBI") may be subject to a sterilization cycle alongside medical devices, e.g., in a STERRAD® System, STERRAD® NX System or STERRAD® 100NX System of Advanced Sterilization Products, Division of Ethicon US, LLC, a Johnson & Johnson company. Following the cycle, the frangible container may be broken to release the growth media and culture any surviving microorganisms in situ. The SCBI may be incubated at elevated temperatures, typically around 50° C. to 60° C., which encourages outgrowth of the surviving microorganisms. Incubation using commercially available products typically lasts for about twenty-four hours. During this time, while the effectiveness of the sterilization remains unconfirmed, it is desirable that medical personnel do not use the medical devices. This may cause inventory management inefficiencies for a health care provider, such as a hospital, because, for example, the medical devices should be stored while they cannot be used, perhaps requiring the health care provider to keep more medical devices in its inventory than it otherwise would to ensure a sufficient supply of medical devices. Alternatively, health care providers may use the medical devices before the incubation is completed and sterilization efficacy confirmed. However, using the medical devices before sterilization efficacy has been confirmed may expose a subject of a medical procedure to risk of infection from the medical devices.

After incubation, the SCBI is analyzed to detect the presence of surviving microorganisms. Should any microorganisms be detected, some SCBIs are designed to incorporate a growth medium that changes color in the presence of microorganisms. If a color change is detected, the sterilization cycle may be considered to have been ineffective. Should no microorganisms be detected, the sterilization cycle may be considered to have been effective. This color change may be due to a shift in pH that occurs due to acid production by live microorganisms that metabolize a growth medium, which also contains a pH indicating dye. Other SCBIs are designed to incorporate a growth medium that includes a fluorophore whose fluorescence depends on the amount of viable microorganisms contained in the medium. For these SCBIs, a color change or change in the amount of fluorescence indicates that surviving microorganisms may have multiplied during incubation.

The frangible container of the SCBI that contains the liquid growth medium is often fabricated from glass. The glass must be sufficiently robust to avoid breakage during transportation, e.g., from the manufacturer of the SCBI to a health care provider. Such robustness, however, corresponds to a greater force required to break the ampule at the desired time by medical personnel. Accordingly, some SCBI manufacturers provide activation devices to hospital personnel to assist them in breaking the ampule.

SUMMARY

The disclosed subject matter is directed to methods of confirming that a biological indicator having an ampule containing a growth medium has been properly activated such that it may be assayed following a sterilization process to confirm that the sterilization process should have been efficacious. The methods may include the steps of depressing a cap of the biological indicator; breaking the ampule; positioning the biological indicator into a biological indicator analyzer having a heating element and a fluorescence sensor, activating the heating element, measuring a first fluorescence intensity of the biological indicator, heating the biological indicator; quenching the fluorescence intensity of the biological indicator from the first fluorescence intensity to a second fluorescence intensity, measuring the second fluorescence intensity; comparing the second fluorescence intensity and first fluorescence intensity to obtain a comparison value; and determining that the comparison value corresponds to a quenching metric of the liquid growth medium. In some embodiments, the step of quenching the fluorescence intensity of the biological indicator includes heating the growth medium and the housing of the biological indicator. In some embodiments, the step of quenching the fluorescence intensity of the biological indicator includes heating the growth medium and the housing of the biological indicator from a temperature of between approximately 22 degrees Celsius and 25 degrees Celsius to a temperature of approximately 57 degrees Celsius. Further, the method may also include a step of cooling the biological indicator prior to the step of positioning the biological indicator into the biological indicator analyzer. In those embodiments where the biological indicator is cooled, the step of quenching the fluorescence intensity of the biological indicator may further include heating the biological indicator. In some embodiments, the comparison value is a difference between the second fluorescence intensity and the first fluorescence intensity. In other embodiments, the comparison value is a ratio of the second fluorescence intensity to the first fluorescence intensity. In some embodiments, the second fluorescence intensity is measured after the first fluorescence intensity. For example, in some embodiments, the second fluorescence intensity is measured approximately 210 seconds after the first fluorescence intensity and the first fluorescence intensity is measured approximately 70 seconds after the biological indicator is positioned in the biological indicator analyzer. Alternatively, the first fluorescence intensity is measured approximately 70 seconds after the heating element of the biological indicator analyzer is activated. In some embodiments the method further includes determining that the first fluorescence intensity value is between a minimum threshold value and a maximum threshold value. For example, in some embodiments, the minimum threshold value is approximately 0.02 $\mu W/cm^2$ and the maximum threshold value is approximately 0.10 $\mu W/cm^2$.

The methods may also include the steps of depressing a cap of the biological indicator; breaking the ampule; positioning the biological indicator into a biological indicator analyzer having a heating element and a fluorescence sensor, activating the heating element, measuring a first fluorescence intensity of the biological indicator, heating the biological indicator; quenching the fluorescence intensity of the biological indicator from the first fluorescence intensity to a second fluorescence intensity, measuring the second fluorescence intensity; comparing the second fluorescence intensity and first fluorescence intensity to obtain a comparison value; and determining that the comparison value does not correspond to a quenching metric of the liquid growth medium. In some embodiments, the step of quenching the fluorescence intensity of the biological indicator includes heating the growth medium and the housing of the biological indicator. In some embodiments, the step of quenching the fluorescence intensity of the biological indicator includes heating the growth medium and the housing of the biological indicator from a temperature of between approximately 22 degrees Celsius and 25 degrees Celsius to a temperature of approximately 57 degrees Celsius. Further, the method may also include a stop of cooling the biological indicator prior to the step of positioning the biological indicator into the biological indicator analyzer. In those embodiments where the biological indicator is cooled, the step of quenching the fluorescence intensity of the biological indicator may further include heating the biological indicator. In some embodiments, the comparison value is a difference between the second fluorescence intensity and the first fluorescence intensity. In other embodiments, the comparison value is a ratio of the second fluorescence intensity to the first fluorescence intensity. In some embodiments, the second fluorescence intensity is measured after the first fluorescence intensity. For example, in some embodiments, the second fluorescence intensity is measured approximately 210 seconds after the first fluorescence intensity and the first fluorescence intensity is measured approximately 70 seconds after the biological indicator is positioned in the biological indicator analyzer. Alternatively, the first fluorescence intensity is measured approximately 70 seconds after the heating element of the biological indicator analyzer is activated. In some embodiments the method further includes determining that the first fluorescence intensity value is between a minimum threshold value and a maximum threshold value. For example, in some embodiments, the minimum threshold value is approximately 0.02 $\mu W/cm^2$ and the maximum threshold value is approximately 0.10 $\mu W/cm^2$.

Biological indicators may have properties and features appropriate for practicing the methods to which the present subject matter is directed. In some embodiments, a biological indicator may include an ampule and a housing, and a liquid growth medium contained in the ampule, wherein the liquid growth medium includes a quencher. In some embodiments, the quench is not oxygen. The quencher may be chosen from the group consisting of aniline, bromobenzene, acrylamide, hydrogen peroxide, imidazole, indole, and succinimide. Alternatively, the quencher may be a metal ion, such as one chosen from the group consisting of $Co^{2+}$, $Ni^{2+}$, $Cu^{2+}$, $Hg^{2+}$, $Pb^{2+}$, $Ag^{+}$, $Cr^{3+}$, and $Fe^{3+}$. In some embodiments the quencher may be oxygen included in the growth medium at a concentration of greater than approximately 37 mg/L. In some embodiments the quencher may be oxygen included in the growth medium at a concentration of greater than approximately 40 mg/L. In some embodiments, the housing of the biological indicator comprises a UV-transparent material. In some embodiments the UV-transparent material comprises quartz. In other embodiments, the UV-transparent material comprises a cyclo olefin.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
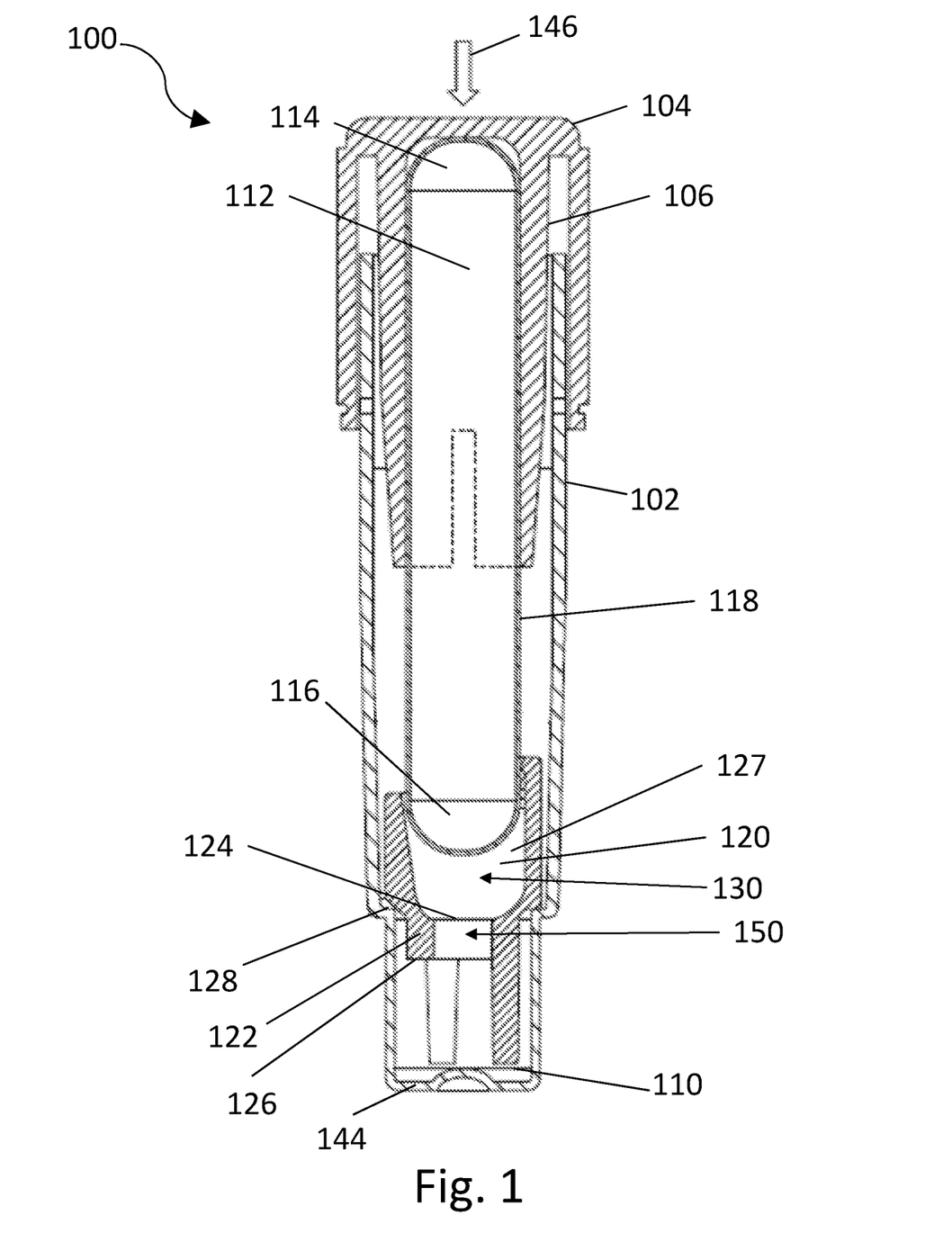
FIG. 1 depicts a side view of a biological indicator in cross-section.
Figure 2:
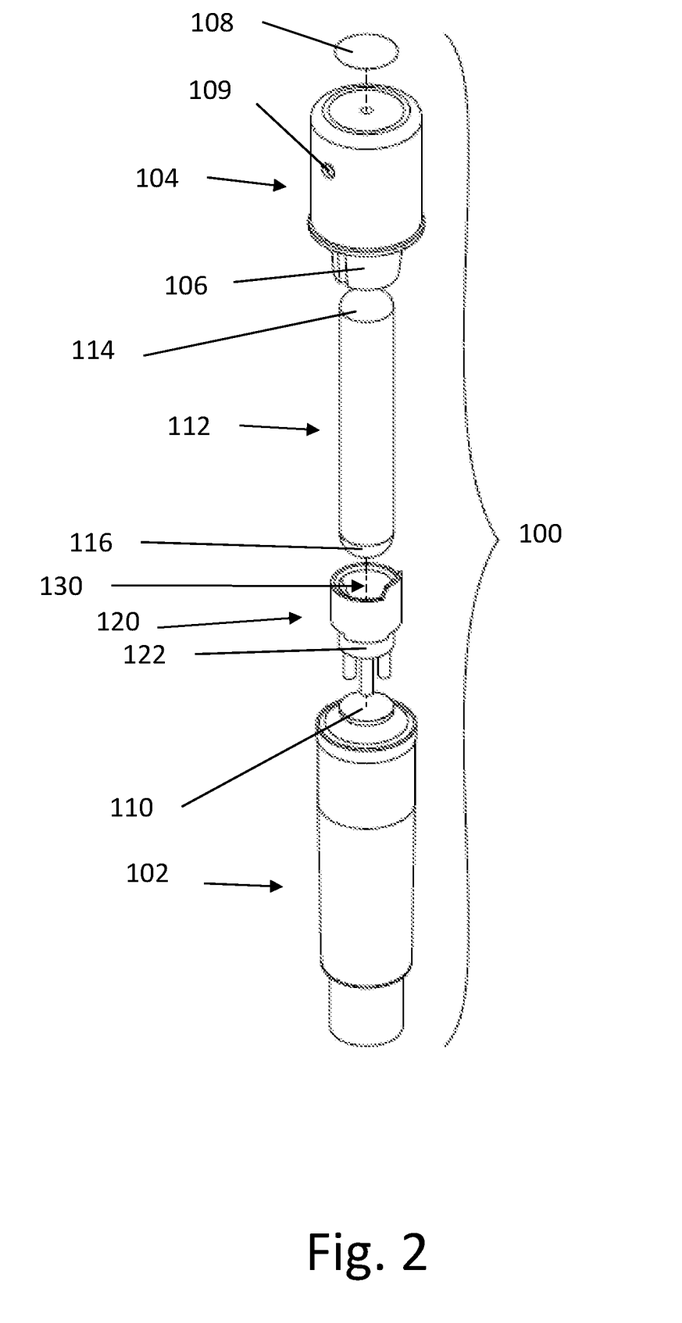
FIG. 2 depicts an exploded view of the biological indicator of FIG. 1.

Referring to FIGS. 1 and 2, a self-contained biological indicator ("SCBI") 100 is shown. SCBI 100 includes a housing 102 and a cap 104 coupled thereto. Cap 104 includes a projection 106 that has a planar, angled, arcuate, annular, or conical shape, or some combination thereof. Cap 104 may further include a chemical indicator 108 that changes color when exposed to, e.g., a chemical sterilant such as hydrogen peroxide. Cap 104 may also include one or more through-holes 109, to assist in the passage of gasses (e.g., air or sterilant) into or out from the SCBI. Cap 104 is coupled relative to housing 102 in a first position and is movable from the first position to a second position. In the first position, cap 104 is coupled to housing 102 in a manner in which gases (e.g., air or sterilant) may move from the surrounding environment and into the SCBI, or vice versa. In this position, any through-holes in cap 104 are disposed above housing 102 such that the inside of housing 102 is in fluid communication with the surrounding environment, which permits introduction and withdrawal of sterilant into and from SCBI 100. Cap 104 may be depressed to move it into the second position relative to housing 102. In this second position, through-holes 109 are disposed below a top end of housing 102, which causes a tight fitting relationship between housing 102 and cap 104, and blocks the through holes, effectively sealing off the inside of the SCBI 100 from the surrounding environment.

SCBI 100 also includes a source of microorganisms or active enzymes, such as carrier 110, which is impregnated with bacterial spores, other forms of bacteria (e.g., vegetative), and/or active enzymes. Spores from *Bacillus, Geobacillus,* and *Clostridia* species are often used to monitor sterilization processes utilizing saturated steam, hydrogen peroxide, dry heat, gamma irradiation and ethylene oxide. Accordingly, carrier 110 may be impregnated with spores from *Bacillus, Geobacillus,* and/or *Clostridia* species. Carrier 110 may be water-absorbent and may be formed of filter paper. Sheet-like materials such as cloth, nonwoven polypropylene, rayon or nylon, and microporous polymeric materials may also be used. Non-water absorbent materials are also appropriate for use, such as metals (e.g., aluminum or stainless steel), glass (e.g., glass beads or glass fibers), porcelain, or plastic. Additionally, carrier 110 can be constructed of a combination of the aforementioned materials. In some embodiments, carrier 110 may have a thickness of approximately 0.1 to 0.5 millimeters.

The microorganism(s) or other source of biological activity on carrier 110 may be chosen based upon the resistance of the source to the particular sterilization process to be used in the sterilization cycle. For example, for a steam sterilization process, *Geobacillus stearothermophilus* or spores thereof, can be used. For an ethylene oxide sterilization process, *Bacillus atrophaeus* (formerly *Bacillus subtilis*), or spores thereof, can be used. In some sterilization processes, sterilization process resistant spores can include, but are not limited to, at least one of *Geobacillus stearothermophilus* spores, *Bacillus subtilis* spores, *Bacillus atrophaeus* spores, *Bacillus megaterium* spores, *Bacillus coagulans* spores, *Clostridium sporogenes* spores, *Bacillus pumilus* spores and combinations thereof.

SCBI 100 also includes an ampule 112, having a first end 114, a second end 116, and a sidewall 118. Sidewall 118 is substantially cylindrical and may have an elliptical or circular cross section. Ampule 112 may be fabricated from a frangible or brittle material such as glass or plastic. First end 114 and second end 116 are disposed at opposite ends of sidewall 118, and may have the form of a hemiellipsoid or hemisphere. Accordingly, first end 114 may be referred to as first dome 114 and second end 116 may be referred to as second dome 116. Ampule 112 contains a liquid growth medium. The growth medium should be capable of promoting growth of any viable microorganisms or other source of biological activity disposed on carrier 110. Preferably, the microorganisms are chosen to generate enzymes that interact with the enzyme substrates to create detectable product, e.g., by having a fluoroscopic intensity or spectrum distinct form the fluoroscopic intensity or spectrum of other materials in SCBI 100. Continued growth of the microorganisms within the growth medium causes an increase in the concentration of the detectable product within the growth medium. In certain embodiments, the detectable product is a fluorophore. Thus, an increase in concentration of the detectable product causes an increase in fluorescence. That is to say, the detectable product is detectable via changes in fluorescence.

Enzymes and enzyme substrates that may be used to detect efficacy of a sterilization cycle are identified in U.S. Pat. No. 5,073,488, entitled "Rapid Method for Determining Efficacy of a Sterilization Cycle and Rapid Read-Out Biological Indicator," issued Dec. 17, 1991, the disclosure of which is incorporated by reference herein; U.S. Pat. No. 5,418,167, entitled "Rapid Read-Out Biological Indicator," issued May 23, 1995, the disclosure of which is incorporated by reference herein; U.S. Pat. No. 5,223,401, entitled "Rapid Read-Out Sterility Indicator," issued Jun. 29, 1993, the disclosure of which is incorporated by reference herein; and U.S. Pat. No. 9,322,046, entitled "Biological Sterilization Indicator," issued Apr. 26, 2016, the disclosure of which is incorporated by reference herein.

Suitable enzymes may include hydrolytic enzymes and/or enzymes derived from spore-forming microorganisms, such as *Bacillus subtilis*. Enzymes from spore-forming microorganisms that can be useful in exemplary biological indicators may include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase, fatty acid esterases and combinations thereof.

In some exemplary methods for determining efficacy of a sterilization cycle as disclosed herein, enzyme substrates are converted to detectable product. For instance, an enzyme substrate may be characterized by a first emission spectrum (e.g., a first fluorescent emission spectrum) and a detectable product may be characterized by a second emission spectrum (e.g., a second fluorescent emission spectrum).

In some exemplary methods for determining efficacy of a sterilization cycle as disclosed herein, suitable enzyme substrates of use may include fluorogenic enzyme substrates. Useful fluorogenic enzyme substrates may be selected from: fluorogenic 4-methylumbelliferyl derivatives (hydrolysable to 4-methylumbelliferone ("4-Mu"), derivatives of 7-amido-4-methyl-coumarin, diacetylfluorescein derivatives, fluorescamine and combinations thereof.

Exemplary 4-methylumbelliferyl derivatives may be selected from: 4-methylumbelliferyl-2-acetamido-4,6-O-benzylidene-2-deoxy-β-D-glucopyranoside, 4-methylumbelliferyl acetate, 4-methylumbelliferyl-N-acetyl-β-D-galactosaminide, 4-methylumbelliferyl-N-acetyl-α-D-glucosaminide, 4-methylumbelliferyl-N-acetyl-β-D-glucosaminide, 2'-(4-methylumbelliferyl)-α-D-N-acetyl neuraminic acid, 4-methylumbelliferyl α-L-arabinofuranoside, 4-methylumbelliferyl α-L-arabinoside, 4-methylumbelliferyl butyrate, 4-methylumbelliferyl 13-D-cellobioside, methylumbelliferyl β-D-N,N' diacetyl chitobioside, 4-methylumbelliferyl elaidate, 4-methylumbelliferyl β-D-fucoside, 4-methylumbelliferyl α-L-fucoside, 4-methylumbelliferyl β-L-fucoside, 4-methylumbelliferyl α-D-galactoside, 4-methylumbelliferyl β-D-galactoside, 4-methylumbelliferyl α-D-glucoside, 4-methylumbelliferyl β-D-glucoside, 4-methylumbelliferyl (3-D-glucuronide, 4-methylumbelliferyl p-guanidinobenzoate, 4-methylumbelliferyl heptanoate, 4-methylumbelliferyl α-D-mannopyranoside, 4-methylumbelliferyl β-D-mannopyranoside, 4-methylumbelliferyl oleate, 4-methylumbelliferyl palmitate, 4-methylumbelliferyl phosphate, 4-methylumbelliferyl propionate, 4-methylumbelliferyl stearate, 4-methylumbelliferyl sulfate, 4-methylumbelliferyl β-D-N,N',N''-triacetyl-chitotriose, 4-methylumbelliferyl 2,3,5-tri-o-benzoyl-α-L-arabinofuranoside, 4-methylumbelliferyl-p-trimethylammonium cinnamate chloride, 4-methylumbelliferyl β-D-xyloside and combinations thereof.

In certain embodiments, the fluorescent response in the SCBI may be based on the naturally occurring alpha-glucosidase enzyme found in the *Geobacillus stearothermophilus* spore coat, which contains the enzyme and which is believed to be important in the germination of *G. stearothermophilus*. Alpha-glucosidase may be used to hydrolyze the bond between the glucose and 4-methylumbelliferyl moieties of 4-methylumbelliferyl α-D-glucopyranoside (α-MUG). α-MUG is not fluorescent. However, following hydrolyzation and separation of the moieties, the 4-Methylumbelliferone (4-MU) product is fluorescent. 4-MU fluoresces when excited by an external energy source, such as a light source that emits light having a wavelength of between approximately 360 and 370 nanometers. So excited, 4-MU emits light having a wavelength of between approximately 440 and 460 nanometers. In certain embodiments, the light source emits light having a wavelength of approximately 365 nanometers and the 4-MU emits light having a wavelength of 450 nm. The fluorescence of 4-MU is pH dependent. For example, when excited by light having a wavelength of 365 nanometers, the intensity of the emitted light is highest at a pH of 10.3. The intensity decreases with pH until about a pH of 7. Below this pH the intensity becomes negligible.

SCBI 100 may also include an insert 120. Insert 120 may include a platform 122 having a top surface 124 and a bottom surface 126. Insert 120 also includes a sidewall 127. Sidewall 127 of platform 122 may rest upon a support surface 128, which may be integrally formed as part of housing 102. Sidewall 127 and top surface 124 of platform 122 together define a well 130, which is configured to receive second end 116 of ampule 112. Platform 122 defines a bore 150 therethrough, through which the liquid growth medium may pass upon breakage of the ampule.

SCBI 100 may be assembled according to the following steps. First, housing 102 is provided. Second, carrier 110 is placed into housing 102 such that it rests upon bottom wall 144 of housing 102. Third, insert 120 is placed into housing 102 such that sidewall 127 of platform 122 rests upon support surface 128. Alternatively, not shown, in some configurations lacking a support surface 128, insert 120 may rest directly upon bottom wall 142 and may be in at least partial contact with carrier 110. Fourth, ampule 112 is inserted into housing 102 such that second end 116 contacts insert 120. Finally, cap 104 is coupled to housing 102 and ampule 112. Projection 106 has approximately the same diameter as ampule 112 such that a friction fit is formed between ampule 112 and projection 106. So assembled, central longitudinal axes of ampule 112, housing 102, cap 104, and insert 120 are coaxial or substantially coaxial. Other assembly procedures may be performed to achieve the same configuration of SCBI 100.

Following a sterilization procedure, an SCBI 100 may be activated and monitored to determine whether a sterilization cycle was effective. To activate SCBI 100, a compressive force 146 is applied between housing 102 and cap 104. This compressive force is resisted by ampule 112 because ampule 112 is in contact with insert 120 and insert 120 is in contact with, e.g., support 128 of housing 102. When the compressive force applied to cap 104 is greater than a breakage force ampule 112 can withstand, ampule 112 will break. Once ampule 112 is broken, cap 104 moves to its second position and growth medium is released to immerse carrier 110.

Various features may be included within the SCBI to facilitate activating the SCBI by, e.g., lowering the force that a user must apply to break the ampule. Exemplary features directed to this functionality are disclosed in copending U.S. patent application Ser. Nos. 15/057,768 and 15/397,018.

Activation of SCBI 100 should be confirmed. For example, activation may be confirmed by, e.g., checking that ampule 112 is broken, that the growth medium submerses carrier 110, that a substantial volume of the growth medium is disposed between bottom surface 126 of insert 120 and bottom wall 144 of housing 102, and/or that cap 104 is in the second position. To increase the likelihood that a failed or improper activation can be detected, multiple checks may be performed. For example, in addition to checking that ampule 112 is broken, submersion of carrier 110 by the growth medium may also be performed. A user or an electromechanical device capable of assaying SCBI 100, such as a biological indicator analyzer ("BIA") 200, may perform these checks. To increase the likelihood that a failed or improper activation can be detected, various checks should be performed by both a user and BIA 200.

Figure 3:
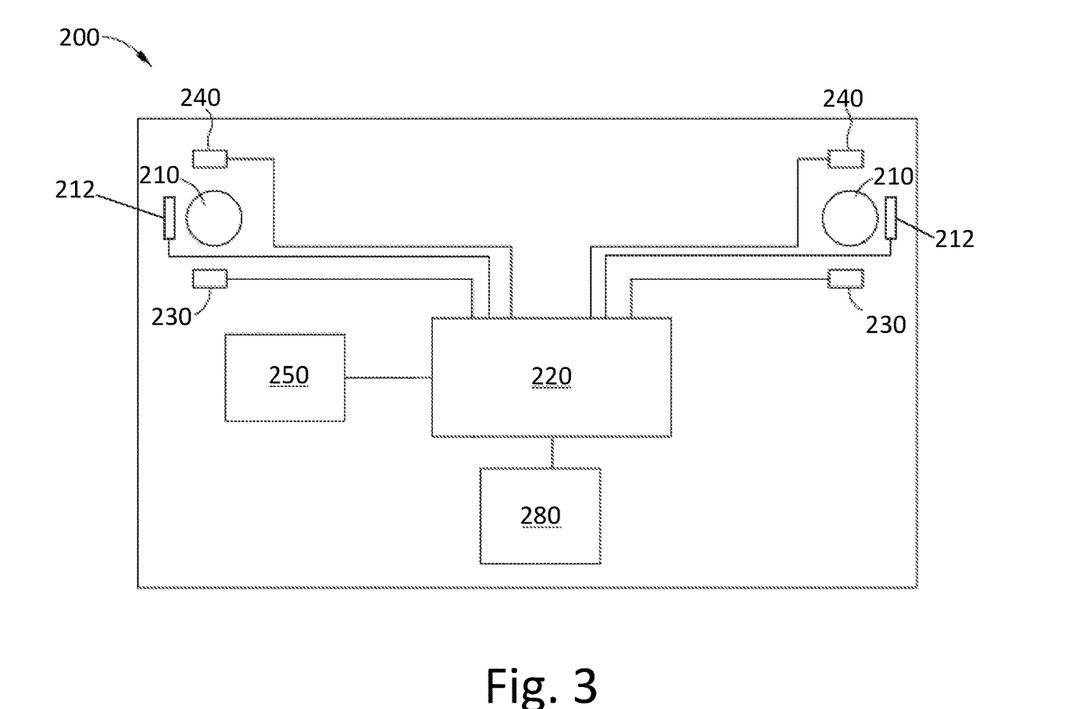
FIG. 3 depicts, in block diagram form, a biological indicator analyzer.

FIG. 3 depicts an exemplary BIA 200 in block form that is operable to analyze a biological indicator, e.g., SCBI 100, which has been subject to a sterilization cycle. BIA 200 is configured to assay an SCBI, collect information about the SCBI (e.g., location of growth medium, color of the growth medium, light intensity of growth medium), process the information, and determine whether the sterilization cycle was effective. BIA 200 comprises a plurality of wells 210, each of which is configured to receive a respective an SCBI 100 specimen therein. While two wells 210 are shown, it should be understood that any other suitable number of wells may be provided, including eight wells, less than eight wells, or more than eight wells. Each well 210 further includes a heating element 212 that can be used to incubate SCBI 100 when it is inserted therein. Such incubation promotes the outgrowth of any live microorganisms within the SCBI. In various embodiments, the heating element may achieve a temperature in the well of between approximately 50° C. and approximately 60° C. In certain embodiments, the heating element may achieve a temperature of approximately 57° C. and cause SCBI 100 to reach a substantially similar or same temperature. BIA 200 also includes a processor 220 that is operable to execute instructions and control algorithms, process information, etc.

Each well 210 has an associated light source 230 and sensor 240. Each light source 230 is configured to project light through housing 102 of the SCBI 100 that is inserted in the corresponding well 210. Each sensor 240 is operable to detect light fluoresced by the growth medium. Each sensor 240 is positioned adjacent to each well 210 such that when an SCBI 100 is disposed within a well, sensor 240 is adjacent to the portion of SCBI 100 between bottom surface 126 of insert 120 and bottom wall 144 of housing 102.

Light source 230 may be in the form of, for example, a laser that is configured to emit ultraviolet light. In some embodiments, the light emitted by light source 230 has a wavelength of 370 nanometers. Various other suitable forms that light source 230 may take will be apparent to those of ordinary skill in the art in view of the teachings herein. By way of further example, sensor 240 may comprise a charge coupled device (CCD). Further, it may be a sensor optimized to detect light generated by fluorescence, i.e., a fluorescence sensor. In some embodiments, sensor 240 is a silicon photodiode, such as silicon photodiode S2386-5K manufactured by Hamamatsu. The fluorescence of the growth medium depends primarily on the number of living microorganisms contained in the growth medium. Thus, sensor 240 is configured to detect the presence of living microorganisms in the growth medium based on the degree to which it fluoresces in response to light from light source 230. However, the fluorescence of the growth medium also depends on whether any fluorescence quenching has occurred. Fluorescence quenching may also be used for confirming proper activation of an SCBI 100, as will be explained in detail below.

BIA 200 optionally further includes a user feedback and/or input device such as touch screen display 250. Touch screen display 250 is operable to render various user interface display screens associated with operation of biological indicator analyzer 200. Touch screen display 250 is further configured to receive user input in the form of the user contacting touch screen display 250 in accordance with conventional touch screen technology. In addition, or in the alternative, biological indicator analyzer 200 may include various other kinds of user input features, including but not limited to buttons, keypads, keyboards, a mouse, a trackball, etc. Displays provided through touch screen display 250 may be driven by processor 220. User inputs received through touch screen display 250 may be processed by processor 220.

BIA 200 of the present example further includes a memory 280, such as non-transitory storage medium (e.g., hard disk drive or a flash memory drive), which is operable to store control logic and instructions and that are executed by processor 220 to drive components such as light source 230 and touch screen display 250 and perform calculations and analyses on data, particularly data collected by sensor 240. Memory 280 may also be used to store user inputs, data collected by sensor 240, and calculations based on this data.

Fluorescence data collected by BIA 200 may be used to determine changes in fluorescence over time. Such data may be used to determine fluorescence quenching. Fluorescence quenching is a term that generally describes various processes that cause the fluorescence intensity of a substance to decrease. For fluorescent substances, such processes include, but are not limited to, 1) heating, 2) lowering pH; and 3) adding another substance or material, sometimes referred as a "quencher," that is known to cause a decrease in fluorescence intensity. Exemplary quenchers include, but are not limited to, oxygen, aniline, bromobenzene, acrylamide, hydrogen peroxide, imidazole, indole, and succinimide. Quenchers may also be metal ions, such as: $Co^{2+}$, $Ni^{2+}$, $Cu^{2+}$, $Hg^{2+}$, $Pb^{2+}$, $Ag^+$, $Cr^{3+}$, and $Fe^{3+}$.

When an SCBI 100 is inserted into a well 210 of BIA 200, its temperature may be substantially equivalent to the ambient temperature, e.g., room temperature. Possibly, however, SCBI 100 may have a temperature warmer than the ambient temperature because vacuum chambers in sterilization systems often are warmer than the ambient temperature at the end of a sterilization cycle. Irrespective of the temperatures of SCBI 100, upon being inserted or shortly after it is inserted into well 210 of BIA 200 (e.g., approximately 1 second, 5 seconds, or 15 seconds), BIA 200 activates heating element 212 to raise the temperature in the well to between approximately 50° C. and approximately 60° C. such that SCBI 100 reaches a substantially similar or same temperature. Heating SCBI 100 in this manner quenches the fluorescence of the components of SCBI 100. Although the quenching is most pronounced in the growth medium, it also may be present, albeit to a lesser degree, in other features of the SCBI 100, i.e., the non-liquid components, including housing 102.

Various components of SCBI 100 may be assayed to determine whether an SCBI 100 has been properly activated. In a properly activated SCBI 100, the growth medium should immerse carrier 110 and be disposed at the bottom of SCBI 100 between bottom surface 126 of insert 120 and bottom wall 144 of housing 102. Accordingly, BIA 200 may assay this portion of SCBI 100 to determine whether the growth medium is present there. For example, BIA 200 may activate light source 230. In certain embodiments, the light emitted by light source 230 has a wavelength of approximately 370 nanometers. If the growth medium is present, the growth medium will be excited and sensor 240 will register a corresponding fluorescence intensity, output a corresponding voltage to processor 220 to be stored in memory 280. However, if the growth medium is not present, the growth medium will not be excited. Nonetheless, the light source may excite other features and materials of SCBI 100 such that sensor 240 will register a corresponding intensity and output a corresponding voltage to processor 220 to be stored in memory 280. The intensity registered by sensor 240 will be different depending on if the growth medium is present in the bottom of an SCBI 100 that has been properly activated or if the growth medium is not present in the bottom of an SCBI 100 that has been improperly activated such that the growth medium remains, e.g., in an unbroken ampule 112, outside of the assay region that light source 230 and sensor 240 can interrogate.

Processor 220 may be programmed to detect the presence of growth medium at the bottom of SCBI 100. In some embodiments, threshold values corresponding to light and/or fluorescence intensities may be stored in memory 280. Specifically, light and/or fluorescence intensities corresponding to a liquid in the bottom of SCBI 100, between bottom surface 126 of insert 120 and bottom wall 144 of housing 102, may be stored in memory 280. By comparing measured intensities to the threshold values, a determination may be made as to whether SCBI 100 was properly activated. For example, processor 220 may be programmed to determine whether a measured intensity falls between a minimum threshold value and a maximum threshold value. An intensity measurement that falls between the threshold values would indicate that growth medium is disposed at the bottom of SCBI 100 and that the SCBI 100 has been properly activated. An intensity measurement that falls below the minimum threshold value would indicate that growth medium is not disposed at the bottom of SCBI 100, likely because it remains in an unbroken ampule 112 due to improper activation. An intensity measurement that falls above the maximum threshold value may indicate a malfunction within BIA 200. In those embodiments where light source 230 provides light having a wavelength of 370 nm, the minimum threshold value may be approximately 0.02 $\mu W/cm^2$ and the maximum threshold value may be 0.10 $\mu W/cm^2$. In those embodiments where sensor 240 is silicon photodiode S2386-5K by Hamamatsu, these minimum and maximum values should be output from sensor 240 as 0.47 volts 2.2 volts, respectively. In some embodiments, the intensity measurement used to confirm proper activation is taken immediately after, or up to approximately 300 seconds after, SCBI 100 is inserted into well 210. In certain embodiments, the intensity measurement is taken approximately 70 seconds after SCBI 100 is inserted into well 210. SCBI activation may be determined in this manner with up to approximately 90%-95% accuracy. Variation in intensity from light source 230 and the temperatures in SCBI 100 maintained by heating element 212 may prevent greater accuracy from being achieved.

Accordingly, it is advisable to supplement this form of confirmation with other methods and forms of confirmation, such as visual confirmation performed by a user, or the following method based on quenching effects of the growth medium and other components of SCBI 100.

Quenching may be determined by calculating a difference or ratio between a first fluorescence-intensity measurement taken at a first time and a second fluorescence-intensity measurement taken at a second time. Quenching effects are typically more pronounced in liquids than solids because molecules in liquids collide more frequently than molecules in solids. Plastic materials, particularly clear or transparent plastic materials commonly used in medical devices, including polycarbonate and cyclo olefin, exhibit a relatively small drop in fluorescence due to heating as compared to colored growth media, including those containing 4-MU, such as those used in SCBI 100. For example, after being heated from room temperature to between 50°-60° and maintained at the higher temperature for about four minutes, the plastic materials exhibit a quenching effect, i.e., a decrease in fluorescence intensity, of between approximately 0 and 5%, whereas the growth medium exhibits a quenching effect between approximately 5% and 25%.

Accordingly, BIA 200, may be used to: 1) take a first fluorescence-intensity measurement at a first time, 2) quench the fluorescence of SCBI 100 by heating SCBI 100, 3) take a second fluorescence-intensity measurement at a second time subsequent to the first time, 4) compare the first fluorescence-intensity measurement with the second fluorescence-intensity measurement by computing a difference or a ratio between the two measurements to determine a degree of quenching, 5) determine whether the degree of quenching corresponds to quenching from only solid or non-liquid components of SCBI 100 or additionally corresponds to quenching from the growth medium, and 6) indicate whether SCBI 100 was improperly activated.

The first fluorescence-intensity measurement may be taken at a first time, i.e., between approximately 0 seconds to approximately 100 seconds after SCBI 100 is inserted into well 210. The second fluorescence-intensity measurement may be taken at a second time, i.e., between approximately 0 seconds to approximately 300 seconds after the first time. In certain embodiments the first time is approximately 70 seconds after SCBI 100 is inserted into well 210 and the second time is approximately 210 seconds after the first time (or 280 seconds after SCBI 100 is inserted into well 210).

The comparison and determination steps may be carried out by processor 220 in various ways. For example, processor 220 may calculate a difference between the second measurement and first measurement and compare the difference to threshold values stored in memory 280 corresponding to degrees of quenching from the solid materials and the growth medium. Alternatively, processor 220 may calculate a ratio between the second measurement and first measurement and compare the ratio to threshold values stored in memory 280 corresponding to degrees of quenching from the solid materials and the growth medium. When BIA 200 performs two checks of activation—one to determine if a single intensity value is between expected minimum and maximum threshold values and another to determine if two intensity values correspond to an expected degree of fluorescence quenching—proper activation may be confirmed with a high degree of accuracy, at least as high as 99%.

The indication step may take the form of processor 220 causing a message to be displayed on display 250 that states whether SCBI 100 was properly or improperly activated. Alternatively or additionally, upon a determination that SCBI 100 was improperly activated, BIA 200 may sound an alarm.

In order to enhance the difference in the degree of quenching the non-liquid components and growth medium undergo when subject to heating, the quenching properties of the non-liquid components and growth medium may be modified. Specifically, the effect of heat on quenching may be increased for the growth medium and decreased for the non-liquid components. Doing so may facilitate differentiating between the non-liquid components and growth medium based on quenching calculations from light-intensity measurements taken by sensor 240. In turn, such modifications may increase the reliability of determinations based on the quenching calculations as to whether SCBI 100 has been properly activated. For example, a quencher, such as aniline, bromobenzene, acrylamide, hydrogen peroxide, imidazole, indole, or succinimide, may be added by, e.g., blending, to the growth medium. Oxygen may also be considered a quencher. The growth medium has an oxygen content of approximately 37 mg/L at sea level. Accordingly, the oxygen content may be increased to approximately 40 mg/L, approximately 45 mg/L or greater to increase the quenching of the growth medium caused by heat. Metal ions may also be considered quenchers. Exemplary metal-ion quenchers include: $Co^{2+}$, $Ni^{2+}$, $Cu^{2+}$, $Hg^{2+}$, $Pb^{2+}$, $Ag^+$, $Cr^{3+}$, and $Fe^{3+}$.

Additionally or alternatively, the growth medium may be modified to have a higher pH. In certain embodiments, the growth medium has a pH between approximately 7.7 and approximately 8.7. In certain embodiments the pH of the growth medium may be approximately 8.2. However, quenching effects are generally maximized at a pH of around 10 because at that pH, fluorescence intensity is also maximized. Accordingly, the pH of the growth medium may be increased to approximately 8.5 approximately 9, approximately 9.5 and approximately 10.

To reduce the amount of quenching in the non-liquid components of SCBI 100 (e.g., housing 102 and insert 120) caused by heat, the non-liquid components may be fabricated from materials having low concentrations of antioxidants, e.g., cyclo olefins, and any other UV-absorbing compounds otherwise found in these components that may absorb UV light from the assay performed by BIA 200. The non-liquid components may also be fabricated from a UV transparent material, such as quartz or low density polyethylene.

Greater increases in temperature may also be utilized to help distinguish between non-liquid components and the growth medium based on quenching measurements. Because the degree of quenching is a function of a change in temperature, a larger change in temperature typically causes greater quenching than a smaller change in temperature. Although such changes affect quenching of the growth medium and the non-liquid components of SCBI 100, changes in temperature have a greater effect on the quenching of the growth medium than the non-liquid components. Therefore, greater accuracy in differentiating between quenching corresponding to non-liquid components and growth media may be achieved by maximizing a temperature difference subject to design constraints relating to assessing microbial growth. Thus, BIA 200 may heat SCBI 100 to temperatures above 60° C. to impart greater quenching effects to SCBI 100, further pronouncing any difference in fluorescence intensity imparted by heating. In a similar vein, BIA 200 may include a cooling element alongside well 210 that may be used to cool SCBI 100 before heating it in order to increase the ultimate change in temperature, and thus, the concomitant quenching effect.

Quenching in the growth medium may be offset by an increase in fluorescence resulting from fluorescent products generated by enzymes in the growth medium. Accordingly, the amount of enzyme generated within the growth medium should be minimized subject to design constraints necessary for determining microbial growth associated with the generated enzyme.

Figure 4:
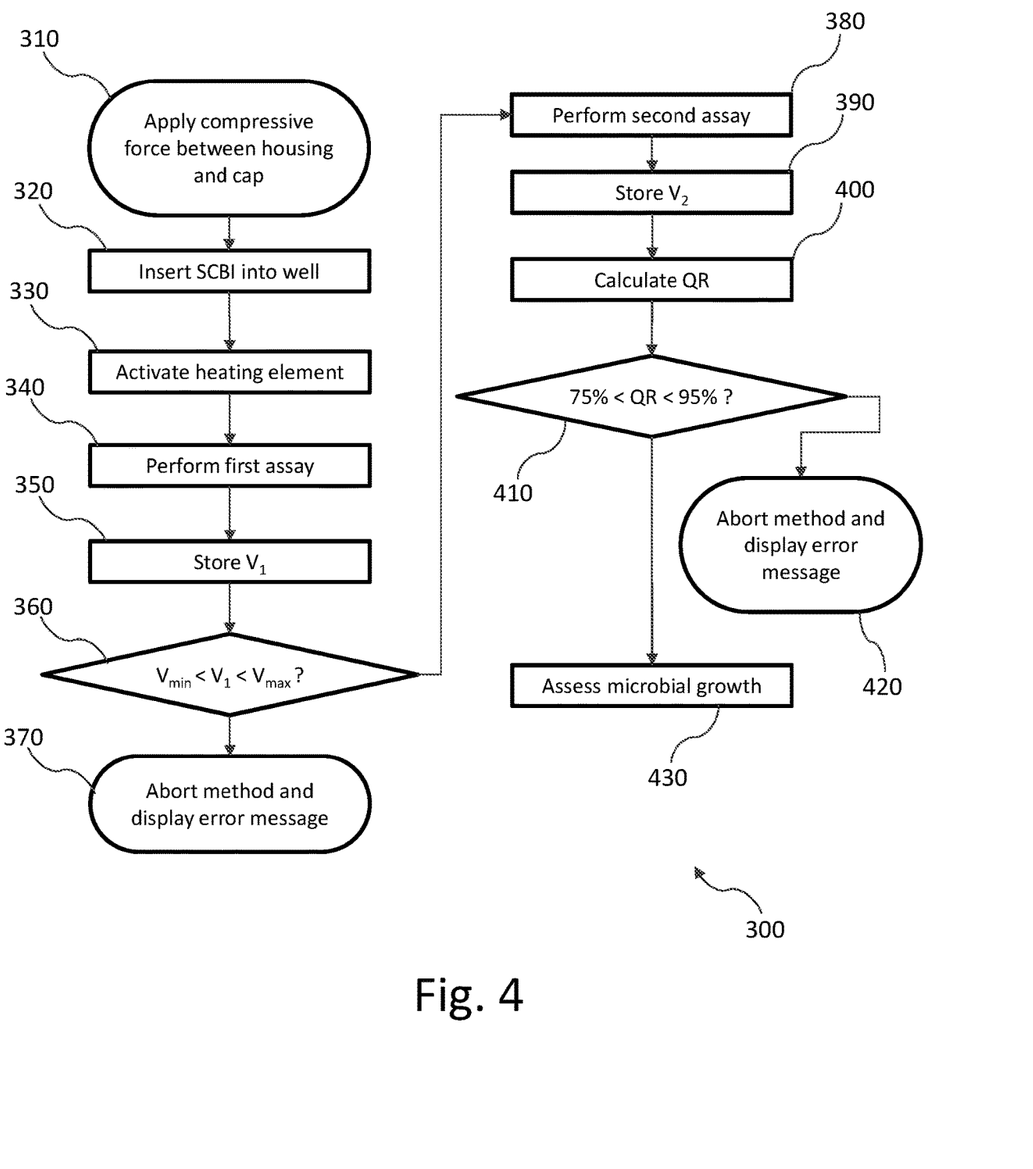
FIG. 4 is a flow diagram of an exemplary method for confirming the activation of a biological indicator of FIGS. 1 and 2 that may be performed by the biological indicator analyzer of FIG. 3.

FIG. 4 depicts a flow chart setting forth an exemplary method 300 for determining whether a biological indicator, such as SCBI 100, has been properly activated according to some of the foregoing teachings. This method may be performed as a part of a larger method (e.g., as a subroutine) in which BIA 200 monitors SCBI for changes in fluorescence caused by microbial outgrowth. Although each and every one of the foregoing teachings are not explicitly incorporated into this example method, it should be understood that those teachings not explicitly set forth may be incorporated into methods for determining activation of biological indicator, such as SCBI 100, based on quenching effects. Furthermore, although SCBI 100, BIA 200, and their components are referenced in presenting this method, it should be understood that the method may be practiced with other biological indicators besides SCBI 100 and other biological indicator analyzers besides BIA 200.

The method 300 begins with step 310 in which a healthcare worker applies compressive force 146 between housing 102 and cap 104 to activate SCBI 100. In typical usage, step 310 occurs after subjecting the SCBI to a sterilization procedure. Successful activation causes cause cap 104 to move from a first position to a second position, thereby breaking ampule 112, which permits the growth medium contained therein to flow to the bottom of SCBI 100, i.e., between bottom surface 126 of insert 120 and bottom wall 144 of housing 102. In step 320, the healthcare worker inserts SCBI 100 into a well 210 of BIA 200. In step 330, BIA 200 activates heating element 212. In step 340, BIA 200 performs a first assay of the bottom of SCBI 100 using light source 230 to excite the SCBI and sensor 240 to measure a first light intensity. Step 340 may be performed between approximately 0 seconds and approximately 100 seconds after step 320. In some embodiments step 340 may occur before step 330. In other embodiments, step 340 may occur after step 330. In some embodiments, step 340 may be performed approximately 70 seconds after step 320, whereas in other embodiments step 340 may be performed approximately 70 seconds after step 330. In step 350, the measured first light intensity, output from sensor 240 as a first voltage value, is stored in storage device 280. In step 360, processor 220 compares the first voltage value ($V_1$) to a minimum threshold voltage value ($V_{min}$) and maximum threshold voltage value ($V_{max}$). In those embodiments where light source 230 emits light having a wavelength of 370 nm and sensor 240 is silicon photodiode S2386-5K manufactured by Hamamatsu, the minimum threshold voltage value may be between approximately 0.4 and approximately 0.5 volts. For example, the minimum threshold voltage value may be approximately 0.47 volts. The maximum threshold voltage value may be between approximately 2.1 and approximately 2.3 volts. For example, the maximum threshold voltage value may be approximately 2.2 volts. If the first voltage value is less than the minimum threshold voltage value or greater than the maximum threshold voltage value, then SCBI 100 may have been improperly activated or BIA 200 may have malfunctioned. Accordingly, in step 370, the method is aborted. An error message may be displayed on display 250 or an alarm may be sounded. If the first voltage value falls between the minimum and maximum threshold values, SCBI 100 may have been properly activated. To confirm whether SCBI 100 was properly activated, BIA 200 continues the method.

BIA 200 performs a second assay of SCBI 100 in step 380. For step 380, BIA 200 uses light source 230 to excite the SCBI and sensor 240 to measure a second light intensity. Step 380 may be performed between approximately 0 second and approximately 300 seconds after step 340. For example, step 380 is performed approximately 210 seconds after step 340 (i.e., approximately 280 seconds after heating element 212 was activated). In step 390, the measured second light intensity, output from sensor 240 as a second voltage value ($V_2$), is stored in storage device 280.

In step 400, processor 220 computes a quenching metric. For example, the quenching metric may be a "quenching difference," i.e., a difference between the second voltage value and the first voltage value or it may take the form of a "quenching ratio," i.e., a ratio between the second voltage value and the first voltage value. If the fluorescence of SCBI 100 has not been quenched, the second voltage value should be equal to or approximately equal to the first voltage value. Accordingly, the quenching difference ("QD") should be equal to or approximately equal to zero and the quenching ratio ("QR") should be equal to or approximately equal to one. As shown in step 400, the quenching metric is the quenching ratio. In step 410, processor determines if there has been minimal quenching (e.g., the quenching ratio is greater than approximately 95%) or substantial quenching (e.g., the quenching ratio is between 75% and 95% when SCBI 100 was heated to approximately 57° C., the first voltage value corresponds to a first light intensity measured approximately 70 seconds after heating element 212 was activated, and the second voltage value corresponds to a second light intensity measured approximately 280 seconds after heating element 212 was activated). Minimal quenching indicates that SCBI 100 was improperly activated because the growth medium should undergo quenching when subject to heat. When processor 220 calculates minimal quenching, step 420 is performed in which the method is aborted. An error message may be displayed on display 250 or an alarm may be sounded. However, when processor 220 calculates substantial quenching, BIA 200 commences its assessment of SCBI 100 according to its primary purpose, i.e., monitoring further changes in fluorescence of the growth medium that may be attributable to microbial growth, as shown in step 430.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method for analyzing a biological indicator including a non-liquid component and an ampule containing a liquid growth medium, the method comprising:
    breaking the ampule;
    positioning the biological indicator into a biological indicator analyzer having a heating element, a light source, and a fluorescence sensor;
    activating the heating element;
    measuring a first fluorescence intensity of the biological indicator;
    quenching the fluorescence intensity of the biological indicator from the first fluorescence intensity to a second fluorescence intensity;
    measuring the second fluorescence intensity;
    calculating a quenching metric from the second fluorescence intensity and the first fluorescence intensity;
    comparing the quenching metric to a threshold value;
    based on comparing the quenching metric to the threshold value, determining that the quenching metric indicates a quenching from the non-liquid component and not the liquid growth medium; and
    in response to determining that the quenching metric indicates a quenching from the non-liquid component and not the liquid growth medium, aborting further monitoring of fluorescence by the biological indicator analyzer
    wherein the quenching metric comprises a quenching ratio or a quenching difference;
    wherein the quenching ratio comprises a ratio of the first fluorescence intensity to the second fluorescence intensity and the step of determining that the quenching metric indicates a quenching from the non-liquid component and not the liquid growth medium includes determining that the quenching ratio is greater than approximately 95%; and
    wherein the quenching difference comprises a difference between the second fluorescence intensity and the first fluorescence intensity and the step of determining that the quenching metric indicates a quenching from the non-liquid component and not the liquid growth medium includes comparing the quenching difference to threshold values corresponding to degrees of quenching from the non-liquid components and the growth medium.

2. The method of claim 1, wherein the step of quenching the fluorescence intensity of the biological indicator includes heating the biological indicator.

3. The method of claim 1, wherein the step of quenching the fluorescence intensity of the biological indicator includes heating the growth medium and the housing of the biological indicator from a temperature of between approximately 22 degrees Celsius and 25 degrees Celsius to a temperature of between approximately 50 degrees Celsius and 60 degrees Celsius.

4. The method of claim 2, further comprising the step of cooling the biological indicator prior to the step of positioning the biological indicator into the biological indicator analyzer.

5. The method of claim 2, wherein the first fluorescence intensity is measured after the heating element is activated and the second fluorescence intensity is measured after the first fluorescence intensity is measured.

6. The method of claim 5, further comprising the step of confirming that the first fluorescence intensity value is between a minimum threshold value and a maximum threshold value.

7. The method of claim 1, wherein the first fluorescence intensity is measured at a time between about 0 seconds and about 100 seconds after the biological indicator is positioned in the biological indicator analyzer and the second fluorescence intensity is measured at a time between about 0 seconds to about 300 seconds after the first time.

8. The method of claim 7, wherein the first time is about 70 seconds after the biological indicator is positioned in the biological indicator analyzer and the second time is about 210 seconds after the first time.

* * * * *

UNITED STATES PATENT AND TRADEMARK OFFICE
CERTIFICATE OF CORRECTION

| | |
|---|---|
| PATENT NO. | : 11,053,534 B2 |
| APPLICATION NO. | : 15/639872 |
| DATED | : July 6, 2021 |
| INVENTOR(S) | : Ben Fryer and Yan Fang |

It is certified that error appears in the above-identified patent and that said Letters Patent is hereby corrected as shown below:

In the Claims

Column 16, Line 3-5, Claim 1: change "wherein the quenching ratio comprises a ratio of the first fluorescence intensity to the second fluorescence intensity" to --wherein the quenching ratio comprises a ratio of the second fluorescence intensity to the first fluorescence intensity--

Signed and Sealed this
Fourteenth Day of February, 2023

Katherine Kelly Vidal
*Director of the United States Patent and Trademark Office*